(12) United States Patent
West et al.

(10) Patent No.: US 7,265,560 B2
(45) Date of Patent: Sep. 4, 2007

(54) TEMPERATURE COMPENSATED VAPOR SENSOR

(75) Inventors: Jeffrey A. West, Bellville, OH (US); Jared Starling, Mansfield, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 0 days.

(21) Appl. No.: 11/286,985

(22) Filed: Nov. 23, 2005

(65) Prior Publication Data

US 2007/0117207 A1    May 24, 2007

(51) Int. Cl.
*G01N 27/04* (2006.01)
*G01R 27/08* (2006.01)

(52) U.S. Cl. ............. 324/721; 324/720; 324/691; 422/95; 422/98

(58) Field of Classification Search ........... 324/720, 324/721; 422/95, 97
See application file for complete search history.

(56) References Cited

U.S. PATENT DOCUMENTS

| | | | |
|---|---|---|---|
| 5,512,450 A * | 4/1996 | Johnson et al. | 435/19 |
| 5,864,458 A * | 1/1999 | Duffy et al. | 361/93.9 |
| 6,747,329 B2 * | 6/2004 | Yoshihara et al. | 257/419 |
| 2005/0285601 A1 * | 12/2005 | Seto | 324/526 |

FOREIGN PATENT DOCUMENTS

| | | |
|---|---|---|
| EP | 0698786 | 2/1996 |
| EP | 1467199 | 10/2004 |
| GB | 1259566 | 1/1972 |
| GB | 1479925 | 7/1977 |
| JP | 54134698 | 10/1979 |
| JP | 06160318 A * | 6/1994 |
| WO | WO2004/048956 | 6/2004 |

OTHER PUBLICATIONS

Communication from the European Patent Office dated Mar. 13, 2007.

* cited by examiner

*Primary Examiner*—Walter Benson
*Assistant Examiner*—John Zhu
(74) *Attorney, Agent, or Firm*—Harness, Dickey & Pierce, PLC

(57) ABSTRACT

A chemiresistor sensor system that compensates for changes in resistance caused by changes in ambient temperature, thereby increasing the accuracy of the sensor system's ability to detect target analytes. The sensor system generally includes a first resistor, a second resistor, and a load regulator or switch that is sensitive to changes in ambient temperature. At least one of the first resistor and the second resistor is a sensing element having a resistance that changes in response to the presence of one or more of the analytes. The switch manages an electrical load across the first resistor and the second resistor. The switch prevents passage of the electrical load across the first and/or second resistor when the ambient temperature is at a first value. The switch permits passage of the electrical load across the first and/or second resistor when the ambient temperature is at a second value.

15 Claims, 2 Drawing Sheets

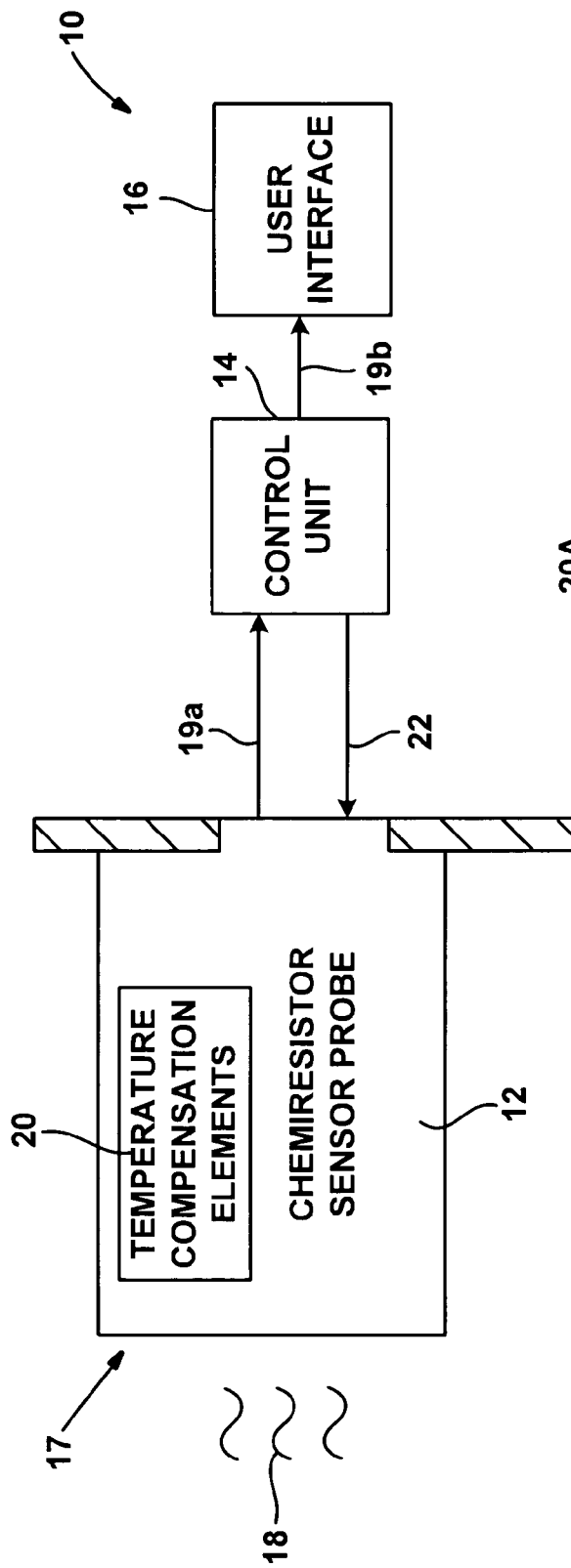
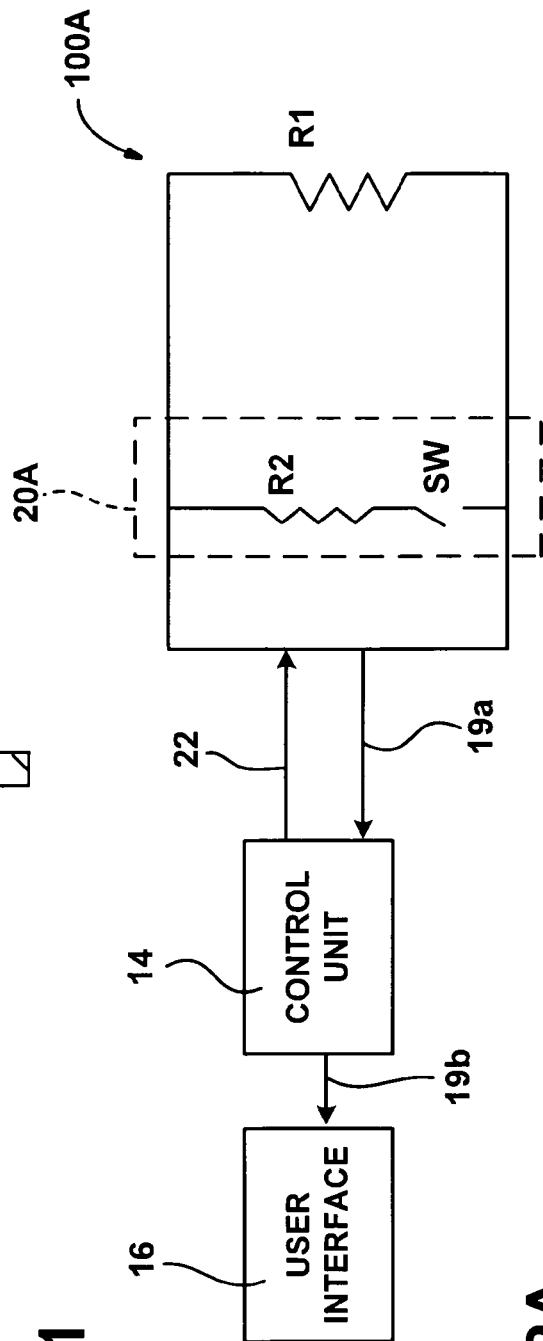
FIG. 1
FIG. 2A

TEMPERATURE COMPENSATED VAPOR SENSOR

FIELD OF THE INVENTION

The present invention relates to chemiresistor sensors. In particular, the present invention relates to a chemiresistor sensor system having multiple resistive elements that can be selectively incorporated into a sensor circuit to change the overall resistance of the circuit in response to changes in ambient temperature.

BACKGROUND OF THE INVENTION

Detecting the presence of specific chemical compounds in the atmosphere is important in a variety of different applications. For example, it is often important to detect the presence and concentration of potentially flammable compounds in the atmosphere. Chemical compounds of interest are often referred to as target analytes.

A variety of different sensor systems known in the art can be used to detect the presence and concentration of different analytes. For example, conductiometric sensor systems, optical sensor systems, and surface acoustic wave sensor systems can all be used.

One type of conductiometric sensor is a polymer-absorption chemiresistor sensor. Polymer-absorption chemiresistor sensors include a sensor probe having a pair of electrodes and a sensing element. The probe is part of a sensor circuit.

The sensing element typically takes the form of a polymeric sensor film that spans the two electrodes. The sensor film is exposed to the surrounding atmosphere. The exact composition of the polymeric sensor film varies depending on the target analyte, as is known in the art, such that the sensor film absorbs the target analyte when it is present in the surrounding atmosphere.

A load is applied across the sensor film via the electrodes. Upon exposure to and absorption of the target analyte, the sensor film swells and undergoes a volumetric change. The change in volume changes the electrical resistance of the film.

A processor or control unit is typically coupled to the sensor circuit. The processor monitors the resistance of the sensor film to determine the absence, presence, and concentration of the target analytes. The processor can be coupled to a user interface. The user interface typically includes an indicating device that generates a signal when the concentration of the target analyte exceeds a predetermined threshold value.

The resistance of the sensor film changes not only in response to absorption of the target analytes, but also in response to changes in ambient temperature. If the sensor film has a positive temperature coefficient of resistance, the resistance of the sensor film increases as ambient temperature increases. If the sensor film has a negative temperature coefficient of resistance, the resistance of the sensor film decreases as ambient temperature increases. Whether the sensor film has a positive or negative temperature coefficient of resistance depends on the composition of the sensor film and the application.

Because detection of target analytes is based on changes in the resistance of the sensor film that occur when the sensor absorbs target analytes, changes in ambient temperature that change the resistance of the sensor film can negatively affect the sensor system's ability to accurately detect the presence of target analytes. For example, if the sensor film has a positive temperature coefficient of resistance and increases in resistance upon the absorption of target analytes, increases in ambient temperature might cause the sensor system to generate a false signal indicating that target analytes are present when they are not.

While conventional chemiresistor sensor systems perform adequately for their intended uses, they are subject to improvement. Specifically, there is a need for a chemiresistor sensor system that can modify its overall resistance in response to changes in ambient temperature to increase the accuracy of the sensor system.

SUMMARY OF THE INVENTION

The sensor system improves upon the prior art by providing a chemiresistor sensor system that compensates for changes in resistance caused by changes in ambient temperature, thereby increasing the accuracy of the sensor system's ability to detect target analytes.

The sensor system generally includes a first resistor, a second resistor, and a load regulator or switch. At least one of the first resistor and the second resistor is a sensing element having a resistance that changes in response to the presence of one or more of the analytes. The resistors also change resistance in response to changes in ambient temperature.

The switch manages an electrical load across the first resistor and the second resistor. The switch prevents passage of the electrical load across the first and/or second resistor(s) when the ambient temperature is at a first value. The switch permits passage of the electrical load across the first and/or second resistor when the ambient temperature is at a second value.

The sensor system advantageously incorporates the first and/or second resistors into a sensing circuit in response to changes in ambient temperature. By selectively incorporating the first and/or second resistors in a variety of different configurations, such as electrically in parallel or in series, the sensor system is able to change its overall resistance to compensate for changes in resistance of the first and second resistors caused by changes in ambient temperature. The sensor system's ability to compensate for changes in resistance caused by changes in ambient temperature increases the system's ability to accurately detect the presence of target analytes.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a block diagram of a chemiresistor sensor system according to the present invention;

FIG. 2A is a simplified schematic diagram showing circuitry of a sensor probe of the sensor system of FIG. 1 according to a first embodiment;

DETAILED DESCRIPTION OF THE PREFERRED EMBODIMENTS

Figure 2B:
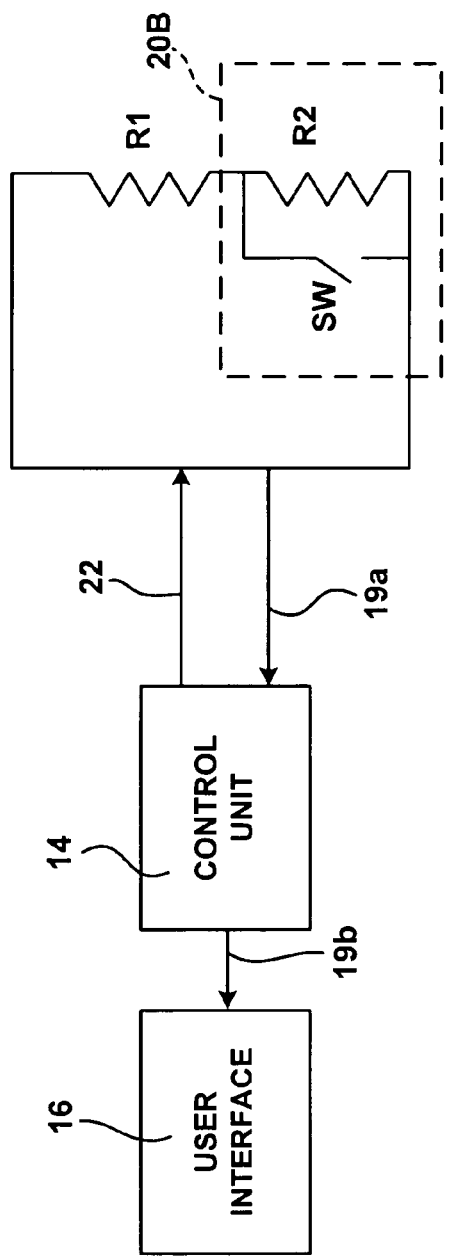
FIG. 2B is a simplified schematic diagram showing circuitry of a sensor probe of the sensor system of FIG. 1 according to a second embodiment.

The following description of the preferred embodiments is merely exemplary in nature and is in no way intended to limit the invention, its application, or uses.

FIG. 1 generally depicts the major components of an exemplary chemiresistor sensor system at 10. The sensor system 10 is generally comprised of a chemiresistor sensor probe 12, a control unit 14, and a user interface 16. The sensor probe 12 includes temperature compensating elements 20.

The sensor probe 12 interacts with an external environment 17 to detect the presence of chemical compositions of interest, or target analytes 18. The sensor probe 12 generates a raw output signal 19a based on continuous detection of analytes 18 in the external environment 17. The raw output signal 19a is processed by the control unit 14. The control unit 14 transmits a calculated output signal 19b to the user interface 16 to relay analysis of the raw output signal 19a from the sensor probe 12. The control unit 14 supplies operating commands and a load, both represented at 22, to the probe 12.

The user interface 16 provides information to a user regarding the status of the sensor system 10, such as whether or not the system 10 detects the presence of the target analytes 18. The user interface 16 can be of a variety of different forms known in the art and can range from a simple alarm signal to a sophisticated computerized display.

The sensor probe 12 can take the form of a variety of different sensor probes. For example, the sensor probe 12 can take the form of any of the sensor probes described in U.S. patent application Ser. No. 10/412,602, titled Robust Chemiresistor Sensor and filed Apr. 11, 2003. U.S. patent application Ser. No. 10/412,602 is hereby incorporated by reference.

The sensor probe 12 includes a conductive sensor element or film. The sensor film can be any suitable sensor film known in the art, such as those described in U.S. patent application Ser. No. 10/411,805, which was filed on Apr. 11, 2003 and is titled "Vapor Sensor and Materials Therefor." The sensor film absorbs the target analytes 18 and changes resistance upon absorbing the target analytes.

With additional reference to FIG. 2, a simplified schematic diagram showing the circuitry of the sensor probe 12 is illustrated at 100.

FIG. 2A illustrates the circuitry of the sensor probe 12 according to a first embodiment at 100A. In the embodiment at 100A, the sensor probe 12 includes a first resistor R1, a second resistor R2, and a load regulating device or switch SW. The second resistor R2 and the switch SW are part of the temperature compensation element 20A.

The first resistor R1 is provided by the sensor film. The second resistor R2 can be a second sensor film or any conventional resistor known in the art. The first resistor R1 and the second resistor R2 are arranged electrically in parallel. The resistance of the circuit 100A is monitored by the control unit 14.

The switch SW is movable between an open position and a closed position. The switch SW opens and closes in response to changes in ambient temperature. The switch SW can be any suitable switch known in the art, such as a stand-alone thermostatically activated switch or a switch controlled by external means. In some embodiments, the switch SW is a bimetal temperature control, such as any one of the 36T series of bimetal temperature controls from Therm-O-Disc Inc. of Mansfield, Ohio, for example.

When the switch SW is in the closed position the second resistor $R_2$ is connected electrically in parallel with the first resistor $R_1$. When the switch SW is in the open position the resistor $R_2$ is removed from the circuit, leaving only the first resistor $R_1$ in the circuit.

An additional embodiment of the circuitry of the sensor probe 12 is illustrated in FIG. 2B at reference numeral 100B. The circuit 100B includes the same elements as the circuit 100A. As with the circuit 100A, the temperature compensation elements 20B include the second resistor $R_2$ and the switch SW. The only substantial difference between the circuit 100A and the circuit 100B is the manner in which the different elements are arranged. Therefore, the general description of the resistors $R_1$ and $R_2$ and the switch SW set forth in connection with the description of the circuit 100A equally applies to the circuit 100B.

In the circuit 100B, the first resistor $R_1$ and the second resistor $R_2$ are arranged electrically in series. The switch SW is positioned to provide a low resistance bypass around the resistor $R_2$. When the switch SW is open the load passes through both the first resistor $R_1$ and the second resistor $R_2$ in series to increase the overall resistance of the circuit 100B. When the switch SW is closed the load bypasses the second resistor $R_2$ to remove the second resistor $R_2$ from the circuit 100B and lower the overall resistance of the circuit 100B.

Figure 2C:
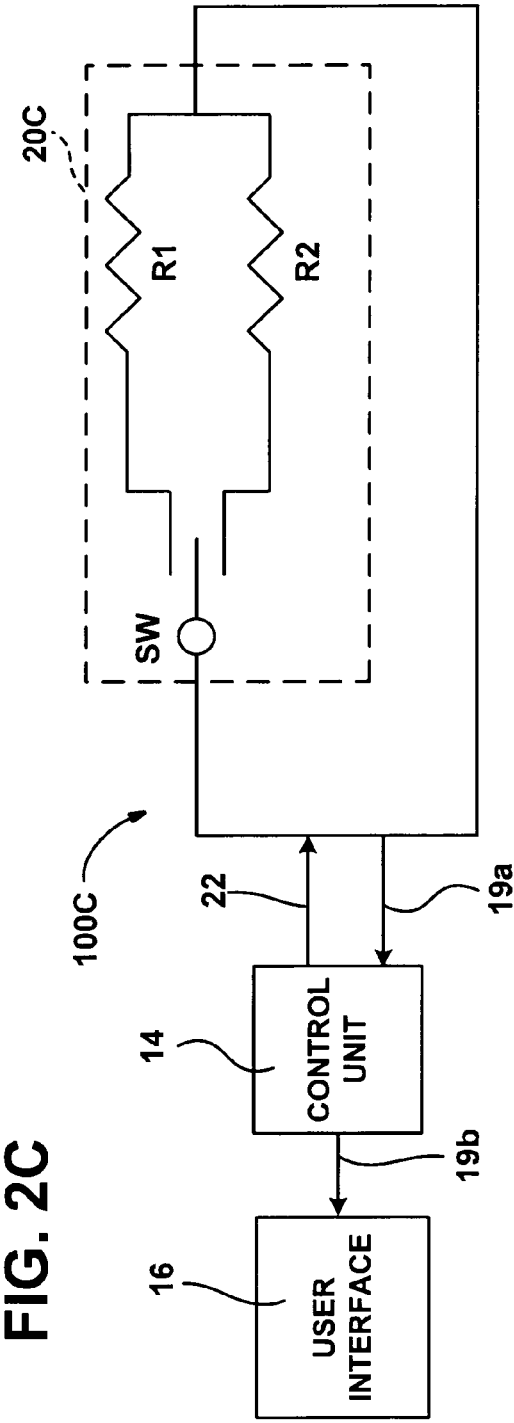
FIG. 2C is a simplified schematic diagram showing circuitry of a sensor probe of the sensor system of FIG. 1 according to a third embodiment.

FIG. 2C illustrates an additional embodiment of the circuitry of the sensor probe 12 at reference numeral 100C. The circuit 100C includes all of the same elements as the circuit 100A. However, in the circuit 100C the second resistor $R_2$, like the first resistor $R_1$, is provided by the sensor film of the probe 12 with the first resistor $R_1$ and the second resistor $R_2$ having different resistances. The temperature compensation elements 20 include the switch SW and both resistors $R_1$ and $R_2$. The general description of the resistor $R_1$ and the switch SW set forth in connection with the description of the circuit 100A equally applies to the circuit 100C.

In the circuit 100C, the first and second resistors $R_1$ and $R_2$ are on independent load paths. Actuation of the switch SW places either the first resistor $R_1$ or the second resistor $R_2$ in the circuit 100C. Specifically, the switch can be moved between a first position in which it contacts the load path of the first resistor $R_1$ to include the first resistor $R_1$ in the circuit 100C and a second position in which it contacts the load path of the second resistor $R_2$ to include the second resistor $R_2$ in the circuit 100C. The first resistor has a first resistance and the second resistor has a second resistance that is lower than the first resistance.

The circuit 100 may take the form of numerous other embodiments in addition to those provided at reference numerals 100A, 100B, and 100C. For example, the circuit 100 can include a combination of series and parallel circuits as well as combinations of positive, negative, and zero temperature coefficient resistors. Any suitable circuit having a plurality of resistors operable to compensate for changes in resistance due to changes in ambient temperature can be used.

Operation of the sensor system 10 will now be described. The target analytes 18 are absorbed by the sensor film of the probe 12 when the analytes 18 are present in the external environment 17. The sensor film swells upon absorption of the analytes 18. As the film swells, the distance between conductive particles embedded in the sensor film increases, thus changing the resistance $R_1$ (or $R_2$ in the circuit 100C) of the film as measured by the control unit 14.

Upon detecting a change in resistance, the control unit 14 transmits a calculated output 19b to the user interface 16 instructing the user interface 16 to alert the user that the target analytes 18 have been detected by the probe 12. The user interface 16 may be any appropriate interface capable of providing an alert to the user. The interface 16 may range in complexity from a simple alarm to a complex computer providing audio and visual alerts.

Operation of the sensor probe 12 outfitted with some of the different sensor circuits 100 set forth herein will now be described.

With respect to the circuit 100A, the switch SW opens and closes in response to changes in ambient temperature. If the first and second resistors $R_1$ and $R_2$ both have a positive temperature coefficient of resistance, such that the resistance increases as temperature increases, the switch SW remains in an open position when the ambient temperature is at or below a predetermined temperature value or threshold. When the switch SW is in the open position only the resistor $R_1$ is in the circuit. Operation of the switch SW can be controlled by the control unit 14 and/or the switch SW can be a stand-alone thermostatically activated switch.

When the ambient temperature rises above the predetermined temperature threshold, the switch SW closes to place the second resistor $R_2$ in parallel with the first resistor $R_1$. Having the first and second resistors $R_1$ and $R_2$ in parallel lowers the overall resistance of the circuit 100A below the individual resistance of the first and second resistors $R_1$ and $R_2$ to take into account the increased resistance of the resistors $R_1$ and $R_2$ caused by the increase in ambient temperature.

When the ambient temperature drops back to or below the predetermined temperature, the switch opens to return the resistance of the circuit 100A to its optimal resistance for the predetermined temperature.

If the first and second resistors $R_1$ and $R_2$ both have a negative temperature coefficient of resistance, such that the resistance decreases as the temperature increases, the operation of the switch SW is reversed. Specifically, the switch SW opens when the ambient temperature rises above the predetermined temperature and closes when the ambient temperature is at or below the predetermined temperature.

With respect to the circuit 100B, the switch SW remains open at or below a predetermined ambient temperature threshold or value so that the first resistor $R_1$ and the second resistor $R_2$ are electrically in series to maintain the overall resistance of the circuit 100B at an acceptable resistance. If the first and second resistors $R_1$ and $R_2$ both have a positive temperature coefficient of resistance, such that the resistance increases as temperature increases, the switch SW closes when the ambient temperature increases above a predetermined temperature threshold. Closing the switch effectively removes the second resistor R2 from the circuit and lowers the overall resistance of the circuit 100B to counteract the increase in resistance caused by the increase in ambient temperature.

If the first and second resistors R1 and R2 both have a negative temperature coefficient of resistance, such that the resistance decreases as the temperature increases, the operation of the switch SW is reversed. Specifically, the switch SW remains closed at standard or lower ambient temperatures and opens when the ambient temperature rises above a predetermined temperature threshold.

With respect to the circuit 100C, if the first and second resistors R1 and R2 each have a positive coefficient of resistance, the switch SW is placed in the first position at or below a predetermined ambient temperature value or threshold to include the first resistor R1 in the circuit 100C. When the ambient temperature rises above the predetermined temperature threshold the switch moves to the second position to remove the first resistor R1 from the circuit and include the second resistor R2 in the circuit. Replacing the first resistor R1 with the second resistor R2 lowers the overall resistance of the circuit 100C because the second resistor R2 has a lower resistance than the first resistor R1.

If the first and second resistors R1 and R2 have a negative temperature coefficient of resistance, the operation of the switch SW in response to changes in ambient temperature is reversed. Specifically, the switch SW moves to the second position when the ambient temperature is at or below the predetermined temperature threshold. The switch moves to the first position when the temperature rises above the predetermined temperature threshold.

The circuits 100 compensate for changes in the resistance of the first and second resistors R1 and R2 that occurs due to changes in ambient temperature. Therefore, the sensor system 10 is able to distinguish between changes in resistance caused by the presence of the target analytes 18 versus changes in resistance caused by changes in ambient temperature. As a result, the sensor system 10 can detect the presence of the analytes 18 with improved accuracy.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A chemiresistor sensor system for detecting the presence of one or more analytes comprising:
    a first resistor;
    a second resistor; and
    a load regulating device that manages an electrical load current across at least one of said first resistor and said second resistor;
    wherein each of said first resistor and said second resistor is a sensing element with a resistance that changes in response to the presence of one or more of the analytes, said sensing element comprising a conductive polymer matrix;
    wherein said load regulating device prevents passage of the electrical load current across said first resistor when the ambient temperature is at a first value; and
    wherein said load regulating device permits passage of the electrical load current across said first resistor when the ambient temperature is at a second value.

2. The chemiresistor sensor system of claim 1, wherein said first resistor is electrically in parallel with said second resistor.

3. The chemiresistor sensor system of claim 1, wherein said first resistor is electrically in series with said second resistor.

4. The chemiresistor sensor system of claim 1, wherein said load regulating device comprises a switch.

5. The chemiresistor sensor system of claim 1, wherein the polymer of said conductive polymer matrix is crosslinked.

6. The chemiresistor sensor system of claim 1, wherein said first value is greater than said second value.

7. The chemiresistor sensor system of claim 1, wherein said first value is less than said second value.

8. A chemiresistor sensor system circuit for detecting the presence of an analyte, said circuit comprising:
- a first sensing element having a first resistance that changes in response to the presence of the analyte, said first sensing element comprising a conductive polymer matrix;
- a second sensing element having a second resistance that changes in response to the presence of the analyte, said second resistance is different from said first resistance, said second sensing element comprising a conductive polymer matrix; and
- a switch;
- wherein said switch incorporates said first sensing element into said circuit and removes said second sensing element from said circuit at a first ambient temperature value;
- wherein said switch incorporates said second sensing element into said circuit and removes said first sensing element from said circuit at a second ambient temperature value that is different from said first ambient temperature value.

9. The chemiresistor sensor system circuit of claim 8, wherein the polymer of said conductive polymer matrix of at least one of said first sensing element and said second sensing element is crosslinked.

10. The chemiresistor sensor system circuit of claim 8, wherein said switch is a stand-alone thermally activated switch.

11. The chemiresistor sensor circuit of claim 8, wherein said switch is a bimetal switch.

12. A method for compensating for the effects of ambient temperature on a chemiresistor sensor circuit system having a first sensing element comprising a conductive polymer matrix with a resistance that changes in response to the presence of one or more analytes, the method comprising:
- determining the ambient temperature of the area surrounding the sensor circuit system;
- actuating a switch to add a second sensing element comprising a conductive polymer matrix if the ambient temperature is at a first value; and
- actuating the switch to remove the second sensing element from the sensing circuit system if the ambient temperature is at a second value that is different from the first value.

13. The method of claim 12, further comprising adding the second sensing element to the sensor circuit system so that the second sensing element is electrically in parallel with the first sensing system.

14. The method of claim 12, further comprising adding the second sensing element to the sensor circuit system so that the second sensing element is electrically in series with the first sensing element.

15. The method of claim 12, wherein said conductive polymer matrix of said second sensing element is crosslinked.

* * * * *

UNITED STATES PATENT AND TRADEMARK OFFICE
CERTIFICATE OF CORRECTION

| | | |
|---|---|---|
| PATENT NO. | : 7,265,560 B2 | Page 1 of 1 |
| APPLICATION NO. | : 11/286985 | |
| DATED | : September 4, 2007 | |
| INVENTOR(S) | : Jeffrey A. West et al. | |

It is certified that error appears in the above-identified patent and that said Letters Patent is hereby corrected as shown below:

Column 8,
Line 20, Claim 13, "sensing system" should be --sensing element--.

Signed and Sealed this

Fourteenth Day of April, 2009

JOHN DOLL
*Acting Director of the United States Patent and Trademark Office*